United States Patent [19]

Karol et al.

[11] Patent Number: 4,548,724

[45] Date of Patent: Oct. 22, 1985

[54] SUCCINIMIDE DERIVATIVES AS ADDITIVES IN LUBRICATING OILS

[75] Inventors: Thomas J. Karol, Wappingers Falls; Rodney L. Sung, Fishkill; Benjamin J. Kaufman, Wappingers Falls, all of N.Y.

[73] Assignee: Texaco Inc., White Plains, N.Y.

[21] Appl. No.: 614,606

[22] Filed: May 29, 1984

[51] Int. Cl.⁴ .............................................. C10M 1/32
[52] U.S. Cl. ................................ 252/51.5 A; 548/564; 260/245.7

[58] Field of Search ................ 252/51.5 A; 548/546; 260/245.7

[56] References Cited

FOREIGN PATENT DOCUMENTS 746520 11/1966 Canada .............................. 548/546

*Primary Examiner*—Jacqueline V. Howard
*Attorney, Agent, or Firm*—Robert A. Kulason; James J. O'Loughlin; Carl G. Seutter

[57] ABSTRACT

Dispersant additives in lubricating oils are formed by reaction of polyacids such as 1,3,6-hexane tricarboxylic acid and polyisobutenyl succinimide of a polyamine.

50 Claims, No Drawings

SUCCINIMIDE DERIVATIVES AS ADDITIVES IN LUBRICATING OILS

FIELD OF THE INVENTION

This invention relates to lubricating oils. More particularly it relates to dispersant additives for lubricating oils.

BACKGROUND OF THE INVENTION

As is well known to those skilled in the art, during operation of internal combustion engines, whether spark or compression ignition, the lubricating oils are contaminated with solids arising from several sources. It is desired to maintain these solids suspended or dispersed in the oil and thus prevent their deposition on the various surfaces and screens with which they come into contact.

Those skilled in the art constantly seek to improve the nature of dispersants used, with respect to various properties including cost of manufacture, seal compatibility, etc,—in addition to dispersant ability.

There is a substantial body of prior art which discloses production of alkenyl succinimides and their use in lubricating oil formulations. Illustrative of these patents may be the following.

U.S. Pat. Nos. 3,287,271; 3,172,892; 4,048,080; 2,568,876; 3,216,936; 3,131,150; 4,338,205; 3,172,892; 3,401,118; Neth Pat. No. 7,509,289 etc.

It is an object of this invention to provide a novel dispersant for use in lubricating oils. Other objects will be apparent to those skilled in the art.

STATEMENT OF THE INVENTION

In accordance with certain of its aspects, this invention is directed to a method which comprises reacting
 (i) a hydrocarbyl-substituted mono- or bis-succinimide bearing a polyamine

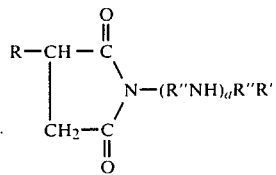

wherein

R is an alkenyl group containing about 8-400 carbon atoms;

R" is a divalent hydrocarbon group selected from the group consisting of alkylene, alkarylene, aralkylene, cycloalkylene, arylene, alkenylene, and alkynylene;

R' is $-NH_2$, $-NHR'''$ or a hydrocarbyl-substituted group:

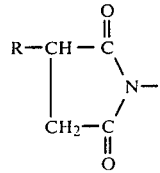

R''' is a hydrocarbon group selected from the group consisting of alkyl, alkaryl, aralkyl, alkenyl, alkynyl, cycloalkyl, and aryl;

with (ii) an organic polycarboxylic acid $R^*(COOH)_x$ wherein x is an integer 3-6; and $R^*$ is a hydrocarbon group derived by removing a-1 hydrogen atoms from an alkyl, alkaryl, aralkyl, cycloalkyl, aryl, alkeny, or alkynyl hydrocarbon group thereby forming product; and recovering said product.

DESCRIPTION OF THE INVENTION

The charge materials which may be employed in practice of the process of this invention include as a first reactant a hydrocarbyl-substituted mono- or bis-succinimide bearing a polyamine

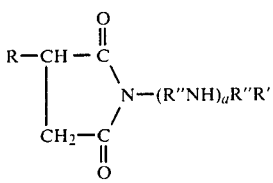

wherein

R is an alkenyl group containing about 8-400 carbon atoms;

R" is a divalent hydrocarbon group selected from the group consisting of alkylene, alkarylene, aralkylene, cycloalkylene, arylene, alkenylene, and alkynylene;

R' is $-NH_2$, $-NHR'''$ or a hydrocarbyl-substituted succinimide group

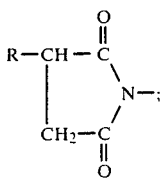

R''' is a hydrocarbon group selected from the group consisting of alkyl, alkaryl, alkaryl, alkenyl, alkynyl, cycloalkyl, and aryl; and a is an integer 1-8.

In the above formula R is an alkenyl group containing about 8-400, preferably 70-170, say about 100-carbon atoms. Preferably R is a polyolefin group of molecular weight $\overline{M}_n$ of 900-2000, preferably 1000-1300, say 1290, containing residual unsaturation formed by polymerizing an olefin. Typical olefins which may be polymerized include ethylene, propylene, butylene, amylene, etc. In the preferred embodiment, R is a polyisobutylene group $(C_4H_8)$ of molecular weight $\overline{M}_n$ of 900-2000.

In the above formula, R" may be a hydrocarbon group selected from the group consisting of alkylene, cycloalkylene, arylene, alkarylene, and alkynylene including such radicals when inertly substituted. When R" is alkylene, it may typically be methylene, ethylene, n-propylene, iso-propylene, n-butylene, sec-butylene, amylene, octylene, decylene, octadecylene, etc. When R" is aralkylene, it may typically be benzylene, beta-phenylethylene, etc. When R" is cycloalkylene, it may typically be cyclohexylene, cycloheptylene, cyclooctylene, 2-methylcycloheptylene, 3-butylcyclohexylene, 3-methylcyclohexylene, etc. When R" is arylene, it may typically be phenylene, naphthylene, etc. When R" is alkarylene, it may typically be tolylene, xylylene, etc. When R" is alkenylene, it may typically be vinylene, allylene, 1-butylene, etc. When R" is alkynylene, it may typically be ethynylene, propynylene, butynylene, etc. R" may be inertly substituted i.e. it may bear non-reactive subsituent such as alkyl, aryl, cycloalkyl, ether, halogen, nitro, etc. Typically inertly substituted R" groups may include, 2-ethoxyethylene, carboethoxymethylene, 4-methyl cyclohexylene, p-chlorophenylene, p-chlorobenzylene, 3-chloro-5-methylphenylene, etc. The preferred R" groups may be lower alkylene i.e. $C_1$–$C_{10}$ alkylene, groups including eg methylene, ethylene, n-propylene, i-propylene, butylene, amylene, hexylene, octylene, decylene, etc. R" may preferably be ethylene —$CH_2CH_2$—.

In the above compound, R'" may be a hydrocarbon group selected from the group consisting of alkyl, aralkyl, cycloalkyl aryl, alkaryl, alkenyl, and alkynyl including such radicals when inertly substituted. When R'" is alkyl, it may typically be methyl, ethyl, n-propyl, iso-propyl, n-butyl, i-butyl, sec-butyl, amyl, octyl, decyl, octadecyl, etc. When R'" is aralkyl, it may typically be benzyl, beta-phenylethyl, etc. When R'" iscycloalkyl, it may typically be cyclohexyl, cycloheptyl, cyclooctyl, 2-methylcyclo-heptyl, 3-butylcyclohexyl, 3-methylcyclohexyl, etc. When R'" is aryl, it may typically be phenyl, naphthyl, etc. When R'" is aryl, it may typically be phenyl, naphthyl, etc. When R'" is alkaryl, it may typically be tolyl, xylyl, etc. When R'" is alkenyl, it may typically be vinyl, allyl, 1-butenyl, etc. When R'" is alkynyl, it may typically be ethynyl, propynyl, butynyl, etc. R'" may be inertly substituted i.e. it may bear a non-reactive substituent such as alkyl, aryl, cycloalkyl, ether, halogen, nitro, etc. Typically inertly substituted R groups may include, 2-ethoxyethyl, carboethoxymethyl, 4-methyl cyclohexyl, p-chlorophenyl, p-chlorobenzyl, 3-chloro-5-methylphenyl, etc. The preferred R'" groups may be lower alkyl, i.e. $C_1$–$C_{10}$ alkyl, groups including eg methyl, ethyl, n-propyl, i-propyl, butyls, amyls, hexyls, octyls, decyls, etc. R'" may preferably be n-propyl.

R' may be —$NH_2$, —NHR'" or a hydrocarbyl substituted group;

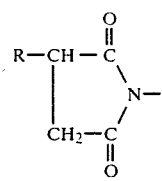

When R' is the noted succinimide group, the first reactant may for example include those of the form

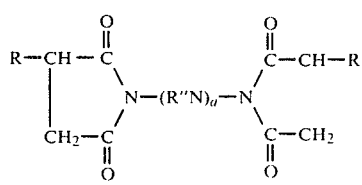

These compounds may be available or readily prepared by the reaction:

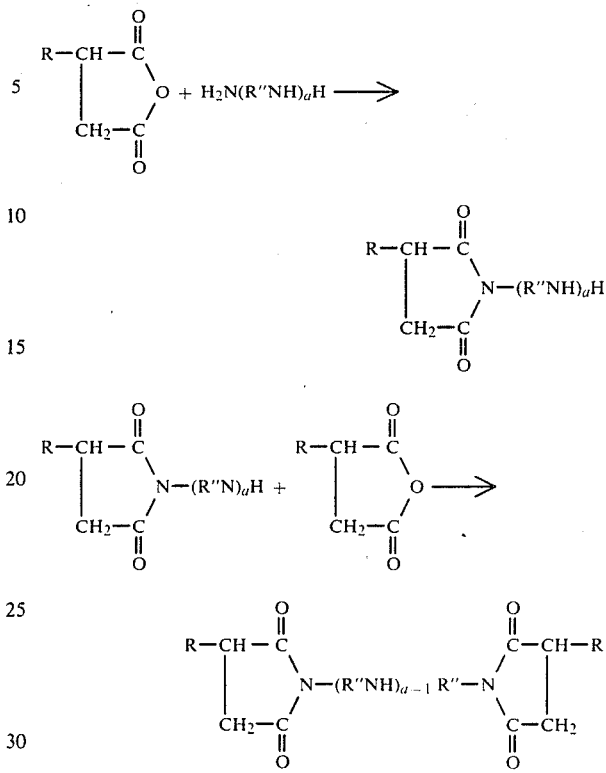

Preferred hydrocarbyl-substituted mono- or bis-succinimides which may be employed include:

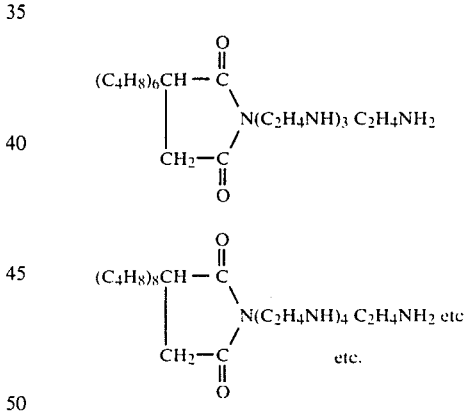

The second reactant may be an organic polycarboxylic acid

wherein x is an integer 3–6, preferably 3. It will be apparent that the polyvalent R* group may be most readily nomenclated with reference to the alkyl group containing the same number of carbon atoms which it most closely resembles but subject to the qualification that (instead of the typical single open valence bond of the alkyl group) it contains x open valence bonds. For example for convenience, an illustrative group may be designated herein as polyvalent n-hexyl (n-hexyl has the standard configuration $CH_3CH_2CH_2CH_2$—$CH_2CH_2$—) and in fact this designation will include eg the following groups inter alia:

```
CH3CHCHCH2CH2CH2—
   |  |
CH2CHCHCH2CH2CH2—
 |  |  |
CH2CHCHCHCH2CH2— etc.
 |  |  |
```

In accordance with this nomenclature, R* may be a hydrocarbon group selected from the group consisting of alkyl, aralkyl, cycloalkyl, aryl, and alkaryl, including such radicals when inertly substituted. When R* is alkyl, it may typically be methyl, ethyl, n-propyl, iso-propyl, n-butyl, i-butyl, sec-butyl, amyl, octyl, decyl, octadecyl, etc. When R* is aralkyl, it may typically be benzyl, beta-phenylethyl, etc. When R* is cycloalkyl, it may typically be cyclohexyl, cycloheptyl, cyclooctyl, 2-methylcyclo-heptyl, 3-butylcyclohexyl, 3-methylcyclohexyl, etc. When R* is aryl, it may typically be phenyl, naphthyl, etc. When R* is alkaryl, it may typically be tolyl, xylyl, etc. R* may be inertly substituted i.e. it may bear a non-reactive substituent such as alkyl, aryl, cycloalkyl, ether, halogen, nitro, etc. Typically inertly substituted R* groups may include 3-chloropropyl, 2-ethoxyethyl, carboethoxymethyl, 4-methyl cyclohexyl, p-chlorophenyl, p-chlorobenzyl, 3-chloro-5-methylphenyl, etc. The preferred R* groups may be alkyl groups having 5–10 carbon atoms, groups including eg amyl, hexyl, octyl, decyl, etc. R* may preferably be hexyl.

Specific typical polyvalent R* groups may include:

TABLE

|   |   |
|---|---|
| CH2CH2CH2CHCH2CH2 <br>       \|      \|    \| | (i) |
| CH2CHCH2CHCH2CH2 <br> \|   \|    \|     \| | (ii) |
| CH3CHCHCH2 | (iii) |
| C6H5CHCHCH2 | (iv) |
| 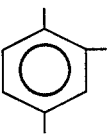 | (v) |
| 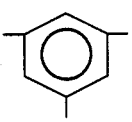 | (vi) |
| 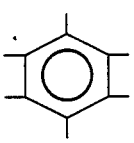 | (vii) |

Illustrative second reactant compounds may include the following:

TABLE

A. 
```
CH2CH2CH2CHCH2CH2COOH
 |              |
COOH          COOH
```

B.
```
CH2  CHCH2CHCH2CH2COOH
 |    |    |
COOH COOH COOH
```

C.
```
CH3CH——CHCH2COOH
   |    |
  COOH COOH
```

D. 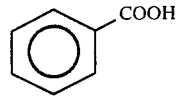  Trimellitic Acid

E.
```
HO—CH—COOH
   |
   CH—COOH
   |
   CH2—COOH
```
isocitric acid

F.
```
CH—COOH
‖
C—COOH
|
CH2—COOH
```
aconitic acid

G.
```
O=C—COOH
   |
   CH—COOH
   |
   CH2—COOH
```
oxalo succinic acid

H. 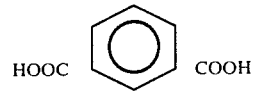  trimesic acid

I. 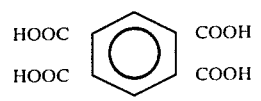  benzene hexacarboxylic acid

J.   hemi-mellitic acid

K. 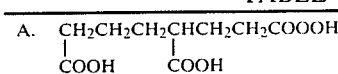  prehnitic acid

L.
```
    C—COOH
    |
HO—C—COOH
    |
    C—COOH
```
citric acid

Reaction may be carried out by adding substantially equivalent quantities of the reactants to the reaction mixture. It will be apparent to those skilled in the art that the equivalent quantities will depend upon (i) the number of nitrogen atoms in the succinimide (ii) the number of carboxyl groups in the second reactant, and (iii) the number of such groups which it is desired to react. It is possible for example to react less than all of the carboxyl groups with the amino groups (and to thus prepare products having free carboxyl groups). In the preferred embodiment however, each of the acid groups will be reacted with an amine group and converted to the corresponding amide groups. Mixtures of acids may be employed.

In view of the nature of the reactants and the plurality of the amine groups and carboxyl groups present, the relative proportions of the reactants may be more clearly determined by the properties of the final product. Generally it is desired that the amount of reactants be controlled so that the resultant product contains the least amount of free acid as measured by total acid number. This is equivalent to saying that the reaction is preferably carried out by using the acid in amount of 20 mole % –90 mole % of the equivalent amount required to react with the amine groups, and by controlling the reaction conditions and time.

By way of illustration, if the charge first reactant N-polyalkyleneamine succinimide contains the grouping

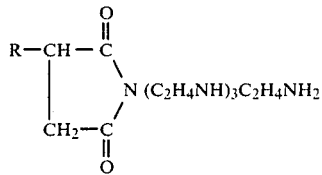

and the second reactant is 1,3,6-trihexanoic acid, then if it be desired to produce the preferred product, the equivalent quantites of reactants may be one mole of each. If one desires to produce e.g. less preferred reaction products containing free carboxyl groups, then greater quantities of the acid will be employed.

It is a particular feature of the process of this invention in its preferred embodiment utilizing 1,3,6-trihexane tricarboxylic acid (also called 1,3,6-trihexanoic acid) that this inexpensive, by-product acid may be used; and since the acid is tribasic, the actual quantity of acid employed is thus typically one-third of the weight of a monobasic acid when preparing a product of comparable molecular weight.

It is also to be noted that improved product characteristics are attained (in terms of the degree of inhibition of deterioration of Viton elastomer seals in an engine) when reaction is carried out so that at least about 30 atom % of the reactive nitrogen atoms in the succinimide chain have been reacted to form an amide with the carboxyl groups of the acid or mixtures of acids. Preferably 50–100 atom %, more preferably 85–100 atom %, say 100 atom % of these nitrogen groups will be reacted; and the final product may thus contain minimal basic nitrogen groups.

In the preferred embodiment of the process of this invention, the succinimide first reactant may be prepared in situ by the reaction of alkenyl succinic acid anhydride and amine $H_2N\,(R''N)_a R''R$, preferably $H_2N\,(R''N)_a R''NH_2$. The preferred mode of operation is to add the anhydride to the reaction mixture as a solution in, or substantially simultaneously with, inert-diluent-solvent. The inert diluent-solvent may include liquid hydrocarbons such as lubricating oil stocks which are compatible with the ultimate lubricating composition in which the additive is to be blended. A preferred diluent-solvent may be the oil 100 E Pale Stock HF present in amount of 50–100 parts, say 100 parts per 100 parts of anhydride.

The reaction mixture may then be preferably warmed to 50° C.–100° C., say 60° C. and placed in an inert atmosphere of typically nitrogen.

The amine is preferably added with agitation. The reaction mixture is then heated to 110° C.–120° C. and maintained at this temperature for 60–120 minutes, say about 60 minutes. A small amount of anti-foamant is added, typically about 0.05 w%, based upon the anhydride, of silicone. There is then added the polycarboxylic acid; and the reaction mixture is heated to 140° C.–180° C., say 160° C. and maintained at that temperature for 4–10 hours, say 8 hours. The product is then filtered hot—at the temperature of reaction; and the so prepared product in diluent-solvent may be utilized without further treatment.

During the course of the reaction, the following may occur:

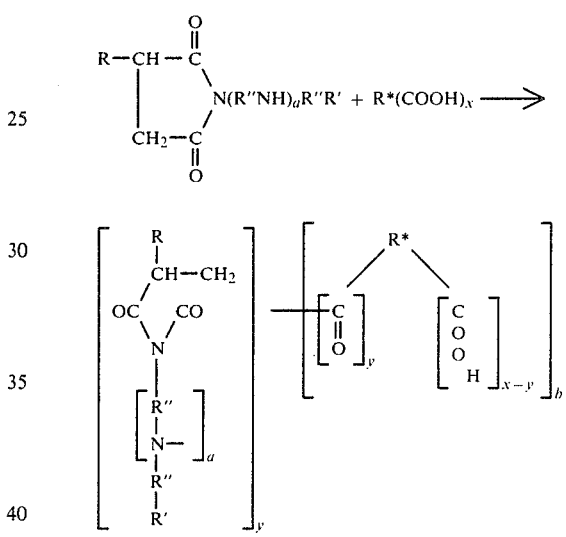

wherein
x is 3–6;
y is 1–3;
a is 0–5;
b is 0.01–3.

In a preferred embodiment wherein 1,3,6-hexane tricarboxylic acid is reacted with the reaction product of a polyisobutylene ($\overline{M}_n$ of 1290) succinic acid anhydride and tetraethylene pentamine, the product may be

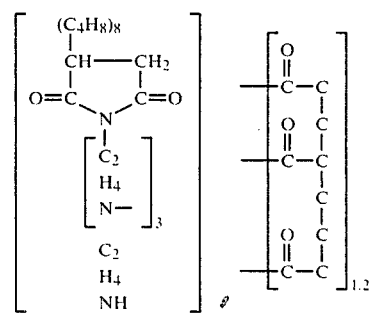

It will be apparent to those skilled in the art that because of the fact that each reactant contains a plurality of reacting groups, the resulting product may not be a simple compound but will undoubtedly include compounds containing an intricate network of products formed as a result of eg different amine group of one molecule of succinimide bonding with a carboxyl group on different molecules of acid and different carboxyl groups of one molecule of acid bonding with an amine group (on different molecules of succinimide).

For these reasons the product will be characterized by the mole ratio of reactants or more commonly by its gross characteristics including molecular weight $\overline{M}_n$, TBN, TAN, and by its ability to serve as eg a dispersant in lubricating oil systems.

The products of this invention may be added to lubricating oil compositions to impart thereto improvements in dispersancy. Typical lubricating oils to which the additives of this invention may be added include summer or winter automotive lubricating oils, airplane engines oils, railway diesel oils, etc. whether hydrocarbon derived or synthetic. Typically the additive may be present in minor effective amount of 0.1-12 w%, preferably 3-8 w%, say 5 w%.

Addition of the additive of this invention to a lubricating oil may be facilitated by use of a concentrate containing 25-95 w%, preferably 50-70 w%, of additive in a diluent-solvent which may in the preferred embodiment be the same as the lubricating oil in which the additive is to be formulated.

It is a feature of the process of this invention that the novel lubricating oils containing a minor effective amount of the additive of this invention may be particularly characterized by their improved dispersancy.

Results attained with the Bench VC Test may typically show that the tested product is as good as or better than the SAE Good Reference Oil.

These products are also characterized by these improved dispersancy as measured by the Bench VD Test. In the Bench VD Test, oil samples are artificially degraded by bubbling air for six hours through a mixture of test oil and synthetic blow-by at 290° F. Every hour synthetic blow-by is added and at the 5th and 6th hour of the test, samples are removed and diluted with SNO-7/20 diluent oil and their turbidity measured. Low turbidity in the BVDT indicates good lubricant dispersancy as related to the Sequence V-D test. Sequence V-D engine correlation work predicts that SF quality lubricants should read 60 or less in the BVDT (turbidity units); oils 70 or greater would be predicted to do significantly poorer in the Sequence V-D Test.

Reference standard: The PV-916-1 reference oil is the only reference standard used in this test. It has had an average Sequence V-D deposit rating of 6.01 = Average varnish, 9.56 = Average sludge. In the BVDT the 6 hour Monitek turbidity should be 55 +/− 12. This reference oil has to be included in each BVD run.

Results attained during the Bench V-D Test typically show that the additives of this invention may be satisfactory dispersants for lubricating oils.

It is a feature of the additives of this invention that they are cost-effective lubricant dispersants which are characterized by a low level of residual acid. The preferred 1,3,6-trihexanoic acid (1,3,6-hexane tricarboxylic acid) is a very inexpensive acid produced as a waste stream; and this permits production of desired product at low cost. It may be desirable to utilize the compositions of this invention (as extenders) in combination with similar composition prepared from more expensive starting materials (eg glycolic acid).

DESCRIPTION OF SPECIFIC EMBODIMENTS

Practice of the process of this invention will be apparent to those skilled in the art from the following wherein, as elsewhere in this description, all parts are parts by weight. Unfiled valence bonds may be filled with hydrogen or with inert substituents.

EXAMPLE I

In this example, 31.6 g (0.167 moles) of tetraethylenepentamine and 384 grams of 100 E Pale Stock HF were charged and nitrogen blanketed. There was then added 400 g (0.185 moles) of polyisobutenyl ($\overline{M}_n$ 1290) succinic acid anhydride having a Sap No. of 51.9 as a 5.9 w% solution in 100 E Pale Stock HF diluent oil. The reaction mixture was then heated to 110° C.–120° C. and maintained at this temperature range for one hour.

There was then added 0.1 ml of silicon oil anti-foamant and 44 g (0.212 moles) of 1,3,6-hexantricarboxylic acid. The reaction mixture was heated to 160° C., removing water as it was formed, and maintained at that temperature for 8 hours. The product was filtered hot.

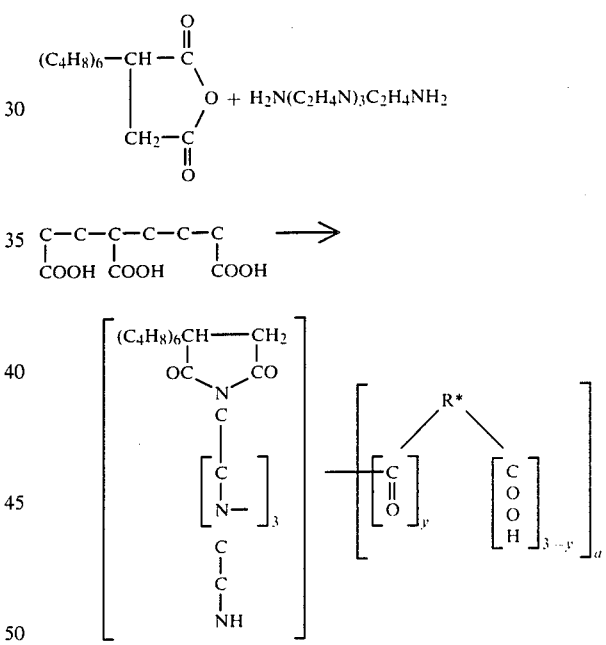

wherein
y is ~2.5 and
a is ca 1.2

EXAMPLE II

| Materials | Grams | Moles |
|---|---|---|
| polyisobutenyl ($\overline{M}_n$ 1290) succinic acid anhydride | 200 | 0.093 |
| tetraethylenepentamine | 11.4 | 0.060 |
| 100 E Pale Stock HF | 187.4 | — |
| 1,3,6-hexane-tricarboxylic acid | 12.5 | 0.060 |
| silicone oil antifoamant 0.05 ml | | |

The procedure of Example I was followed using the above charge materials in the quantities noted—except that the reaction mixture was heated to 60° C. immediately after the anhydride and the Pale Stock were charged.

The product of the reaction is:

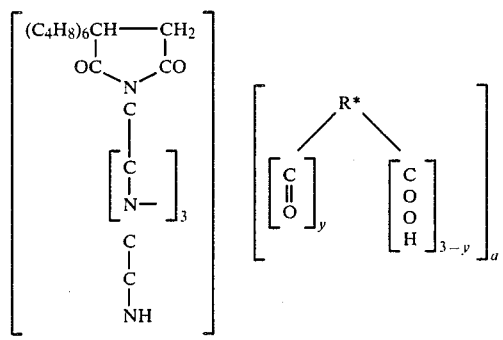

wherein
y is ca 2.5 and
a is ca 1.25.

The reaction mixture may also contain about 50 w% of $$\left[ \begin{array}{c} (C_4H_8)_6-CH-CH_2 \\ OC\diagdown N \diagup CO \\ \left[ \begin{array}{c} C \\ C \\ N \end{array} \right]_3 \\ C \\ C \\ OC\diagdown N \diagup CO \\ (C_4H_8)_6-CH-CH_2 \end{array} \right] \left[ \begin{array}{c} R^* \\ \left[ \begin{array}{c} C \\ \| \\ O \end{array} \right]_y \left[ \begin{array}{c} C \\ O \\ O \\ H \end{array} \right]_{3-y} \end{array} \right]_a$$

wherein
y is ca 2.5 and
a is ca 0.85.

EXAMPLE III

| Materials | Grams | Moles |
|---|---|---|
| polyisobutenyl ($\overline{M}_n$ 1290) succinic acid anhydride | 200 | 0.093 |
| commercial petaethylenehexamine | 15.6 | 0.060 |
| 100 E Pale Stock HF | 191.6 | — |
| 1,3,6-hexane-tricarboxylic acid | 14.9 | 0.072 |
| silcone oil antifoamant 0.05 ml | | |

The procedure of Example II was followed.
The reaction mixture contains:

$$\left[ \begin{array}{c} (C_4H_8)_6CH-CH_2 \\ OC\diagdown N \diagup CO \\ \left[ \begin{array}{c} C \\ C \\ N- \end{array} \right]_4 \\ C \\ C \\ NH \end{array} \right] \left[ \begin{array}{c} R^* \\ \left[ \begin{array}{c} C \\ \| \\ O \end{array} \right]_y \left[ \begin{array}{c} C \\ O \\ O \\ H \end{array} \right]_{3-y} \end{array} \right]_a$$

wherein
y is ca 2.5 and
a is ca 1.2.

The reaction mixture also contains 50 w% of the analogue containing two succinimide rings wherein y is ca 2.5 and a is ca 1.

EXAMPLE IV

| Materials | Grams | Moles |
|---|---|---|
| polyisobutenyl ($\overline{M}_n$ 1290) succinic acid anhydride | 200 | 0.138 |
| pentaethylenehexamine | 23.3 | 0.090 |
| 100 E Pale Stock HF | 223.3 | — |
| 1,3,6-hexane-tricarboxylic acid | 22.4 | 0.108 |

The procedure of Example II was followed.
The product of the reaction is:

$$\left[ \begin{array}{c} (C_4H_8)_6CH-CH_2 \\ OC\diagdown N \diagup CO \\ \left[ \begin{array}{c} C \\ C \\ N- \end{array} \right]_4 \\ C \\ C \\ NH \end{array} \right] \left[ \begin{array}{c} R^* \\ \left[ \begin{array}{c} C \\ \| \\ O \end{array} \right]_y \left[ \begin{array}{c} C \\ O \\ O \\ H \end{array} \right]_{3-y} \end{array} \right]_a$$

wherein
y is ca 2.5 and
a is ca 1.2.

The reaction mixture also contains Ca 50 w% of the analogue containing two succinimide rings wherein y is ca 2.5 and a is ca 0.85.

These products were analyzed for % nitrogen, Total Base Number TBN by ASTM D-2896 and Total Acid Number by ASTM D-974.

| Example | % N | TBN | TAN |
|---|---|---|---|
| I | 1.17 | 17.2 | 10.3 |
| II | 0.95 | 13.0 | 11.1 |
| III | 1.15 | 21.5 | 12.1 |
| IV | 1.58 | 3.03 | 9.70 |

Further tests were made by addition of the noted products to a standard oil based on SNO 20 G and SNO 5.

EXAMPLE V-VIII

In the following examples, the products of examples I-IV were blended (at 8 w% level) into the noted Base Oil and tested for (i) ASTM color by ASTM D-1500; and (ii) Luminescence Turbidity.

TABLE

| Example | Product of Example | ASTM Color | Lum. Turbidity |
|---------|--------------------|------------|----------------|
| V       | I                  | L3.0       | 1.0            |
| VI      | II                 | L6.0       | 2.5            |
| VII     | III                | L3.5       | 2.0            |
| VIII    | IV                 | L3.5       | 4.5            |

L = less than

EXAMPLE IX

The formulation of Example V was also subjected to the Bench L-38 test for corrosion evaluation against ASTM Reference Oils (low) REO 176 and (high) REO 177. The experimental was rated at 41.6; the low reference oil was rated at 32.9 and the high at 82.6. This indicates that the additive is a good candidate for use as a lubricant dispersant—especially when used with other amidated dispersant compositions.

EXAMPLES X-XXIII

In this series of Examples, formulations of the products of Examples I-IV (containing 4 w%, 5 w%, 6 w%, and 8 w%) were made up in the noted Base Oil. The formulations were tested for dispersancy in the Bench VC Test. Also tested were standard SAE good (PV-914), fair (FREO 200-3), and poor (PV-911) reference oil formulations.

TABLE

| Example | Product of Example | 4%   | 5%   | 6%   | 8%   | Good | Fair | Poor |
|---------|--------------------|------|------|------|------|------|------|------|
| X       | I                  | —    | 13.8 | 17.6 | 12.4 | 13.3 | 48.3 | 74.9 |
| XI      | I                  | —    | 16.3 | 12.7 | 9.6  |      |      |      |
| XII     | I                  | 22.5 | —    | 20.6 | 12.4 | 22.9 | 50.9 | 70.9 |
| XIII    | I                  | 25.2 | —    | 19.7 | 12.7 |      |      |      |
| XIV     | II                 | 21.8 | —    | 19.1 | —    | 22.9 | 50.9 | 70.9 |
| XV      | II                 | 25.3 | —    | 19.3 | —    |      |      |      |
| XVI     | II                 |      |      |      | 17.8 | 15.8 | 42.8 | 60.3 |
| XVII    | II                 |      |      |      | 18.8 |      |      |      |
| XVIII   | III                | 21.6 |      | 20.3 |      | 22.9 | 50.9 | 70.9 |
| XIX     | III                | 22.2 | 23.4 |      |      |      |      |      |
| XX      | III                |      |      |      | 13.9 | 15.8 | 42.8 | 60.3 |
| XXI     | III                |      |      |      | 11.3 |      |      |      |
| XXII    | IV                 | 22.7 |      | 14.8 | 15.1 | 22.9 | 50.9 | 70.9 |
| XXIII   | IV                 | 24.6 |      | 16.7 | 16.7 |      |      |      |

From the above table, it is apparent that the products of this invention exhibited good dispersancy by this test.

EXAMPLES XXIV-XXVII

In a further series of examples, formulations were made up in the noted base oil and tested in the Bench V-D Test.

TABLE

| Example | Additive | Ratio of Amine to Anhydride | N-content of blend (w %) | Result |
|---------|----------|------------------------------|--------------------------|--------|
| XXIV    | A        | 0.9                          | 0.08                     | N 155  |
| XXV     | B        | 0.9                          | 0.089                    | N 105  |
| XXVI    | B        | 0.9                          | 0.08                     | N 76   |
| XXVII   | Ex. I    | 0.9                          | 0.8                      | N 40   |

TABLE-continued

| Example | Additive | Ratio of Amine to Anhydride | N-content of blend (w %) | Result |
|---------|----------|------------------------------|--------------------------|--------|
| XXVIII  | Ex. I    | 0.9                          | 0.8                      | N 40   |

A - tetraethylenepentamine glycamide succinimide;
B - pentaethylenehexamine glycamide succinimide From the above table, it is apparent that the products of this invention exhibited excellent dispersancy by this test.

EXAMPLE XXVIII

In this example, 400 g (0.185 moles) of polyisobutenyl ($\overline{M}_n$ 1290) succinic acid anhydride and 383 g of 100 E Pale Stock HF were charged and nitrogen blanketed. 31.3 g (0.65 moles) of ethylene hexamine were added with agitation. The reaction mixture was heated to 110° C.-120° C. and maintained at that temperature for one hour. Silicone antifoamant (0.1 ml) was added followed by 23 g of citric acid. The reaction mixture was heated to 160° C. and maintained for 8 hours. The product was filtered hot.

EXAMPLE XXIX

In this example, the procedure of Example XXVIII was repeated using trimellitic acid in place of citric acid at an equal weight replacement.

EXAMPLE XXX

In this example, the products of Examples XXVIII and XXIX were analyzed for % nitrogen, TAN (by ASTM D-974), TBN (by ASTM D-2896) and in the BVCT (at 6% in the base oil L noted above. The reference oils rated 16.1 (PV 914 Good), 39.0 (FREO 200-3 Fair), and 58.0 (PV 911 Poor).

TABLE

|            | EXAMPLE XXVIII | EXAMPLE XXIX |
|------------|----------------|--------------|
| % N        | 1.19           | 1.13         |
| TAN        | 4.66           | —            |
| TBN        | 20.7           | 27.1         |
| BVCT @ 6%  | 16.0           | 11.0         |

Although this invention has been illustrated by reference to specific embodiments, it will be apparent to those skilled in the art that various changes and modifications may be made which clearly fall within the scope of this invention.

What is claimed is:

1. The method which comprises reacting
   (i) a hydrocarbyl-substituted mono- or bis-succinimide bearing a polyamine

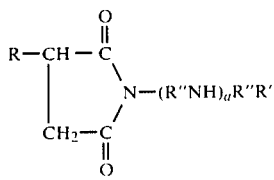

wherein
R is an alkenyl group containing about 8-400 carbon atoms;
R" is a divalent hydrocarbon group selected from the group consisting of alkylene, alkarylene, aralkylene, cycloalkylene, arylene, alkenylene, and alkynylene R' is —NH₂, —NHR''', or a hydrocarbyl-substituted succinimide group

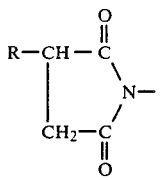

R''' is a hydrocarbon group selected from the group consisting of alkyl, alkaryl, alkaryl, alkenyl, alkynyl, cycloalkyl, and aryl;

a is an integer 1–8 with (ii) an organic polycarboxylic acid R* (COOH)$_x$ wherein x is an integer 3–6; and R* is a hydrocarbon group derived from removing a-1 hydrogen atoms from an alkyl, alkaryl, aralkyl, cycloalkyl, aryl, alkenyl, or alkynyl hydrocarbon group thereby forming product; and recovering said product.

2. The method of claim 1 wherein said succinimide is a polyisobutylene-substituted succinimide.

3. The method of claim 2 wherein said polyisobutylene moiety contains about 8–400 carbon atoms.

4. The method of claim 2 wherein said polyisobutylene moiety has a molecular weight $\overline{M}_n$ of 900–2000.

5. The method of claim 1 wherein said R' is —NH₂.

6. The method of claim 1 wherein said R'' is —CH₂CH₂—.

7. The method of claim 1 wherein said succinimide is

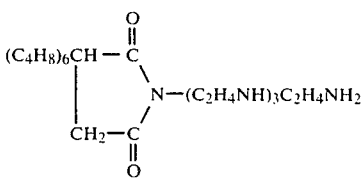

8. The method of claim 1 wherein said R* is a polyvalent hexyl group.

9. The method of claim 1 wherein said x is 3.

10. The method of claim 1 wherein said organic polycarboxylic acid is 1,3,6-hexane tricarboxylic acid.

11. The method of claim 1 wherein said organic polycarboxylic acid is citric acid.

12. The method of claim 1 wherein said organic polycarboxylic acid is trimellitic acid.

13. The method of claim 1 wherein said reaction is carried out in the presence of inert diluent-solvent.

14. The method of claim 1 wherein said reaction is carried out with an amount of acid which is at least equivalent to the active amine groups present in the succinimide bearing a polyamine chain.

15. The method which comprises reacting
(i) as first reactant

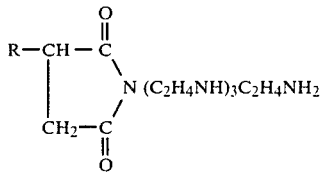

wherein R is a polyolefin group containing about 8–400 carbon atoms with (ii) as second reactant 1,3,6-hexane tricarboxylic acid thereby forming product; and recovering said product.

16. A product prepared by the method which comprises reacting
(i) a hydrocarbyl-substituted mono- or bis-succinimide bearing polyamine

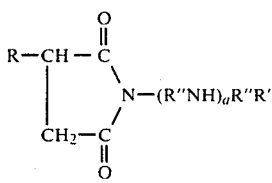

wherein

R is an alkenyl group containing about 8–400 carbon atoms

R'' is a divalent hydrocarbon group selected from the group consisting of alkylene, alkarylene, aralkylene, cycloalkylene, arylene, alkenylene, and alkynlene R' is —NH₂, —NHR''' or a hydrocarbyl-substituted succinimide group

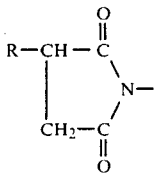

R''' is a hydrocarbon group selected from the group consisting of alkyl, alkaryl, alkaryl, alkenyl, alkynyl, cycloalkyl, and aryl;

a is an integer 1–8 with (ii) an organic polycarboyxlic acid R* (COOH)$_x$ wherein x is an integer 3–6; and R* is a hydrocarbon group derived by removing a-1 hydrogen atoms from an alkyl, alkaryl, aralkyl, cycloalkyl, aryl, alkenyl, or alkynyl hydrocarbon group with (ii) as second reactant 1,3,6-hexane tricarboxylic acid thereby forming product; and recovering said product.

17. A product as claimed in claim 16 wherein said succinimide is a polyisobutylene-substituted succinimide.

18. A product as claimed in claim 17 wherein said polyisobutylene moiety contains about 8–400 carbon atoms.

19. A product as claimed in claim 17 wherein said polyisobutylene moiety has a molecular weight $\overline{M}_n$ of 900-2000.

20. A product as claimed in claim 16 wherein said R' is —NH$_2$.

21. A product as claimed in claim 16 wherein said R" is —CH$_2$CH$_2$—.

22. A product as claimed in claim 16 wherein said succinimide is $$(C_4H_8)_6CH-\overset{O}{\underset{}{\overset{\|}{C}}}\diagdown$$
$$\phantom{(C_4H_8)_6CH}\phantom{-C}\phantom{\diagdown}N—(C_2H_4NH)_3C_2H_4NH_2$$
$$\phantom{(C_4H_8)_6}CH_2—\underset{O}{\overset{}{\underset{\|}{C}}}\diagup$$

23. A product as claimed in claim 16 wherein said R* is a polyvalent hexyl group.

24. A product as claimed in claim 16 wherein said x is 3.

25. A product as claimed in claim 16 wherein said organic polycarboxylic acid is 1,3,6-hexane tricarboxylic acid.

26. A product as claimed in claim 16 wherein said organic polycarboxylic acid is citric acid.

27. A product as claimed in claim 16 wherein said organic polycarboxylic acid is trimellitic acid.

28. A product as claimed in claim 16 wherein said reaction is carried out in the presence of inert diluent-solvent.

29. A product as claimed in claim 16 wherein said reaction is carried out with an amount of acid which is at least equivalent to the active amine groups present in the succinimide bearing a polyamine chain.

30. A product prepared by the method which comprises reacting (i) as first reactant $$R—CH—\overset{O}{\overset{\|}{C}}\diagdown$$
$$\phantom{R—CH}\phantom{-C}\phantom{\diagdown}N\ (C_2H_4NH)_3C_2H_4NH_2$$
$$CH_2—\underset{O}{\underset{\|}{C}}\diagup$$

wherein R is a polyolefin group containing about 8-400 carbon atoms with
(ii) as second reactant 1,3,6-hexane tricarboxylic acid
thereby forming product; and
recovering said product.

31. A product $$\left[\begin{array}{c} R \\ | \\ CH——CH_2 \\ | \phantom{xxx} | \\ OC\diagdown \phantom{x} \diagup CO \\ N \\ | \\ \left[\begin{array}{c} R' \\ | \\ N— \\ | \\ R" \\ | \\ R' \end{array}\right]_a \end{array}\right]_y \left[\begin{array}{c} R^* \\ \diagup \diagdown \\ \left[\begin{array}{c} C \\ \| \\ O \end{array}\right]_y \left[\begin{array}{c} C \\ O \\ O \\ H \end{array}\right]_{3-y} \end{array}\right]_b$$

wherein y is 1-3;
x is 3-6;
a is 0-5; and
b is 0.01-3.

32. A product $$\left[\begin{array}{c} (C_4H_8)_8 \\ | \\ CH——CH_2 \\ | \phantom{xxx} | \\ OC\diagdown \phantom{x} \diagup CO \\ N \\ | \\ \left[\begin{array}{c} C_2 \\ H_4 \\ N— \\ | \\ C_2 \\ H_4 \\ NH \end{array}\right]_3 \end{array}\right]_1 \left[\begin{array}{c} O \\ \| \\ -C-C \\ | \\ C \\ O \\ \| \\ -C-C \\ | \\ C \\ O \\ \| \\ -C-C \\ | \\ O \\ \| \\ -C-C \end{array}\right]_{1.2}$$

33. A lubricating composition comprising a major portion of a lubricating oil and a minor effective dispersancy-improving portion, as an additive, of the product prepared by reaction of
(i) a hydrocarbyl-substituted mono- or bis-succinimide bearing polyamine $$R—CH—\overset{O}{\overset{\|}{C}}\diagdown$$
$$\phantom{R—CH}\phantom{-C}\phantom{\diagdown}N—(R"NH)_aR"R'$$
$$CH_2—\underset{O}{\underset{\|}{C}}\diagup$$

wherein
R is an alkenyl group containing about 8-400 carbon atoms
R" is a divalent hydrocarbon group selected from the group consisting of alkylene, alkarylene, aralkylene, cycloalkylene, arylene, alkenylene, and alkynylene
R' is —NH$_2$, —NHR''' or a hydrocarbyl-substituted succinimide group $$R—CH—\overset{O}{\overset{\|}{C}}\diagdown$$
$$\phantom{R—CH}\phantom{-C}\phantom{\diagdown}N—$$
$$CH_2—\underset{O}{\underset{\|}{C}}\diagup$$

R''' is a hydrocarbon group selected from the group consisting of alkyl, alkaryl, alkaryl, alkenyl, alkynyl, cycloakyl, and aryl;
a is an integer 1-8 with
(ii) an organic polycarboyxlic acid R* (COOH)$_x$
wherein
x is an integer 3-6; and
R* is a hydrocarbon group derived by removing a-1 hydrogen atoms from an alkyl, alkaryl, aralkyl, cycloalkyl, aryl, alkenyl, or alkynyl hydrocarbon group
thereby forming product; and
recoverying said product.

34. A lubricating composition as claimed in 33 wherein said succinimide is a polyisobutylene-substituted succinimide.

35. A lubricating composition as claimed in 34 wherein said polyisobutylene moiety contains about 8–400 carbon atoms.

36. A lubricating composition as claimed in 34 wherein said polyisobutylene moiety has a molecular weight $\overline{M}_n$ of 900–2000.

37. A lubricating composition as claimed in 33 wherein said R' is NH$_2$.

38. A lubricating composition as claimed in 33 wherein said R" is —CH$_2$CH$_2$—.

39. A lubricating composition as claimed in 33 wherein said succinimide is

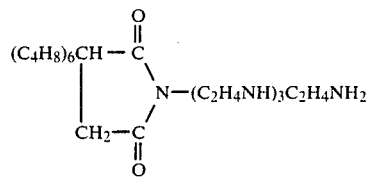

40. A lubricating composition as claimed in 33 wherein said R* is a polyvalent hexyl group.

41. A lubricating composition as claimed in 33 wherein said x is 3.

42. A lubricating composition as claimed in 33 wherein said organic polycarboxylic acid is 1,3,6-hexane tricarboxylic acid.

43. A lubricating composition as claimed in 33 wherein said organic polycarboxylic acid is citric acid.

44. A lubricating composition as claimed in 33 wherein said organic polycarboxylic acid is trimellitic acid.

45. A lubricating composition as claimed in 33 wherein said reaction is carried out in the presence of inert diluent-solvent.

46. A lubricating composition as claimed in 33 wherein said reactions is carried out with an amount of acid which is at least equivalent to the active amine groups present in the succinimide bearing a polyamine chain.

47. A lubricating composition as claimed in 33 wherein said additive is present in a minor effective amount of 0.01–12 w% of said lubricating composition.

48. A lubricating composition as claimed in 33 wherein said additives prepared by reacting
(i) as first reactant

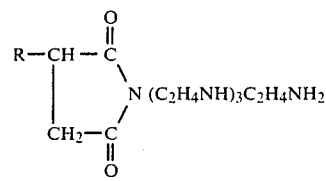

wherein R is a polyolefin group containing about 8–400 carbon atoms with
(ii) as second reactant 1,3,6-hexane tricarboxylic acid thereby forming product; and
recovering said product.

49. A lubricating composition as claimed in 33 wherein said additives is

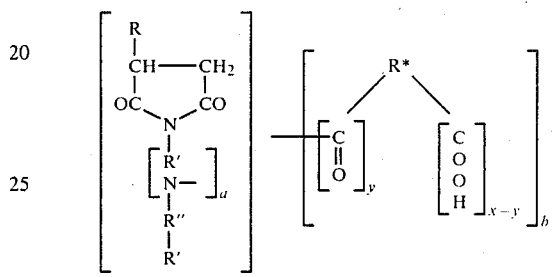

wherein
y is 1–3;
x is 3–6
a is 0–5; and
b is 0.01–3.

50. A lubricating composition as claimed in 33 wherein said additive is

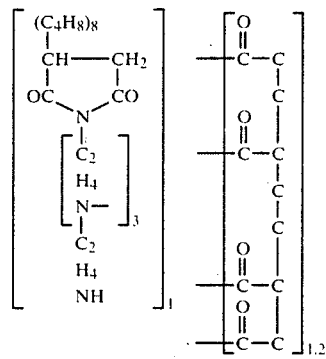

* * * * *